(12) United States Patent
Tait et al.

(10) Patent No.: US 9,744,190 B2
(45) Date of Patent: Aug. 29, 2017

(54) CONTINUOUS GAS GENERATOR

(71) Applicants: Thomas Tait, Box Elder, SD (US); William Moon, Provo, UT (US)

(72) Inventors: Thomas Tait, Box Elder, SD (US); William Moon, Provo, UT (US)

(*) Notice: Subject to any disclaimer, the term of this patent is extended or adjusted under 35 U.S.C. 154(b) by 0 days.

(21) Appl. No.: 14/996,685

(22) Filed: Jan. 15, 2016

(65) Prior Publication Data

US 2017/0202873 A1    Jul. 20, 2017

(51) Int. Cl.
| | |
|---|---|
| *A61K 33/00* | (2006.01) |
| *A61K 9/46* | (2006.01) |
| *A61M 16/12* | (2006.01) |
| *B01J 7/00* | (2006.01) |
| *C01B 21/24* | (2006.01) |
| *A61K 9/00* | (2006.01) |

(52) U.S. Cl.
CPC ............. *A61K 33/00* (2013.01); *A61K 9/007* (2013.01); *A61M 16/122* (2014.02); *B01J 7/00* (2013.01); *C01B 21/24* (2013.01); *A61M 2202/0275* (2013.01)

(58) Field of Classification Search
None
See application file for complete search history.

(56) References Cited

U.S. PATENT DOCUMENTS

| | | | | |
|---|---|---|---|---|
| 4,209,491 | A * | 6/1980 | Rich, III | ............ B01J 7/00 128/202.26 |
| 5,485,827 | A | 1/1996 | Zapol | |
| 5,873,359 | A | 2/1999 | Zapol | |
| 7,178,831 | B2 | 2/2007 | Yoshida | |
| 2004/0038642 | A1 | 2/2004 | Gatley | |
| 2004/0047801 | A1* | 3/2004 | Petillo | ............ B01J 7/02 423/657 |
| 2007/0274874 | A1* | 11/2007 | Miller | ............ B01J 7/00 422/164 |

FOREIGN PATENT DOCUMENTS

WO    WO 2013173303 A1 *  11/2013    ............ C01B 3/04

* cited by examiner

*Primary Examiner* — Susan Tran
*Assistant Examiner* — William Craigo
(74) *Attorney, Agent, or Firm* — Tran & Associates

(57) ABSTRACT

Systems and methods are disclosed for generating a gas at therapeutic levels to a subject by providing a pellet dispenser that delivers a predetermined amount of thermally labile compound to a furnace; controlling a rate of compound addition to allow controlled continuous evolution of the gas; and maintaining a predetermined concentration of the gas using temperature and dilution with an inert gas.

5 Claims, 4 Drawing Sheets

CONTINUOUS GAS GENERATOR

BACKGROUND

The present invention relates to a continuous gas generation system.

Industrial gases are a group of gases that are specifically manufactured for use in a wide range of industries, which include oil and gas, petrochemicals, chemicals, power, mining, steelmaking, metals, environmental protection, medicine, pharmaceuticals, biotechnology, food, water, fertilizers, nuclear power, electronics and aerospace.

The principal gases are nitrogen, oxygen, carbon dioxide, argon, hydrogen, helium and acetylene; although a huge variety of gases and mixtures are available in gas cylinders. The industry producing these gases is known as the Industrial Gases industry and is a part of the wider Chemical Industry (where industrial gases are often seen as "specialty chemicals"). Many applications such as medical applications demand a tight control of cost, volume and quality in the production of the gases.

BRIEF DESCRIPTION OF THE DRAWINGS

The foregoing and other objects, features and advantages of the invention will be apparent from the following more particular description of preferred embodiments of the invention, as illustrated in the accompanying drawings, in which.

SUMMARY

Figure 1:
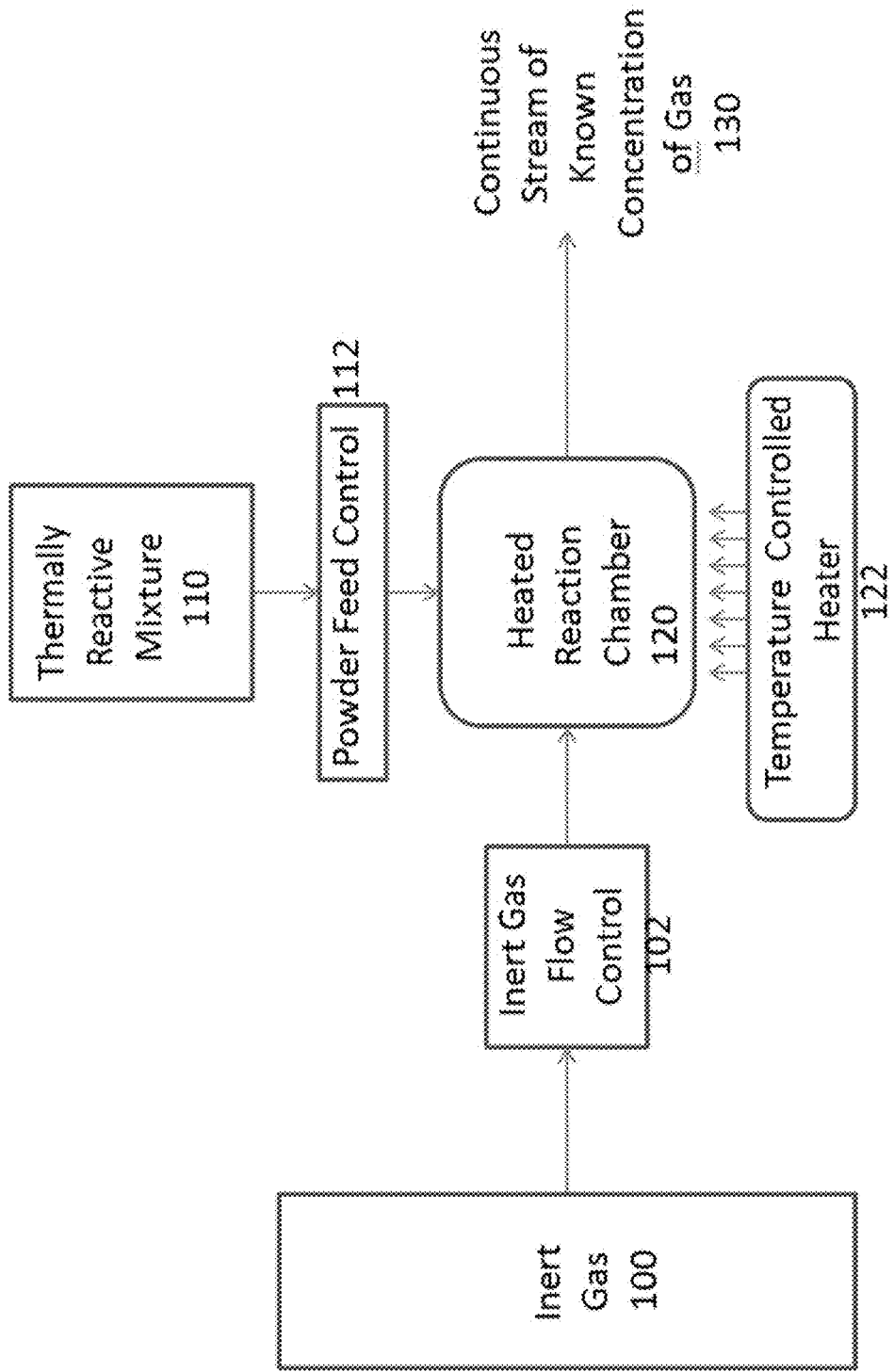
FIG. 1 shows a first exemplary system to continuously release gas.

In one aspect, systems and methods are disclosed for generating a gas at therapeutic levels to a subject by providing a pellet dispenser that delivers a predetermined amount of thermally labile compound to a furnace; controlling a rate of compound addition to allow controlled continuous evolution of the gas; and maintaining a predetermined concentration of the gas using temperature and dilution with an inert gas.

In another aspect, a gas delivery system includes a pellet delivery unit that drops a specified amount of thermally labile compound into a temperature controlled gas generation furnace to generate a pure gas; a timer to control timed addition of thermally labile compound to achieve continuous evolution of gas; a temperature sensor to monitor the furnace temperature; and a dispenser that provides a carrier gas to dilute the pure gas generated from a heated zone.

In a further aspect, a method includes using a diluting gas such as nitrogen to allow control of the nitric oxide concentrations to safe and therapeutic levels. The method of dilution includes pre-diluting the nitric oxide with nitrogen and filling a pressurized steel tank. The diluted nitric oxide gas is stored in pressurized tanks that are part of the medical apparatus. In one implementation, nitric oxide is a gas used in the treatment of several medical conditions.

In yet another aspect, an exemplary system for generating gas is disclosed. The powder feed control adds powder to the heated reaction chamber at a specified rate. The powder begins to react and evolve gas. At a predetermined time the rate of the powder introduction will create a steady state of evolving gas with respect to mass per unit time. The flow of inert gas can now sweep the evolving gas out of the reaction chamber to be used in another process or instrument. By varying the flow of the inert gas with a flow controller the final concentration can be varied and set to a desired number. The process is continuous. Powder is added to the feed hopper and inert gas tanks are replaced as needed.

Advantages of the system may include one or more of the following. The system is direct generation method using thermally labile compounds to produce high purity nitric oxide gas. By controlling the addition of reagents to the gas generation furnace a continuous flow of a specified concentration can be achieved. It also allows the delivery system to use a concentrated gas thereby reducing the size of the equipment and creating a potentially portable device. The system provides continuous generation and dispensing of therapeutic levels of medical gases for inhalation by patients. In one embodiment, the system continuously generates and delivers a specified dose of medical gas over time to a patient via inhalation. to control the administration and concentration of drugs via inhalation for the treatment of various medical conditions.

DESCRIPTION

Systems and methods will be described that allows the continuous, controlled generation of a gas from a solid using thermal energy. The purpose of the device is to provide a continuous stream of a compound or mixture of compounds in the gas state of known concentration over time that can be used in other processes or devices.

The system includes a mechanism that controls the addition of a powdered thermally reactive mixture or compound into a heated reaction chamber at a specified temperature that causes the reactant(s) to undergo a chemical reaction to generate a compound or mixture of compounds in the gas state. The rate of powder feed is adjusted as well as the temperature of the chamber to produce the desired initial rate of gas evolution. An inert gas (relative to the gas produced) flows through the sealed chamber at a specified flow rate to produce a final desired concentration of gas products. By varying these three parameters, powder feed rate, temperature and inert gas flow a concentration steady state can be achieved without regard to the reaction kinetics.

FIG. 1 shows one embodiment of a system to produce a continuous stream of known concentration of gas 130. Inert gas 100 is provided to an inert gas flow control 102. The inert gas flow is delivered into a reaction chamber 120. Inert gases are also known as the noble gases and are mainly the group 8 elements in the periodic table, they have little or no ability to react chemically or in the atmosphere. Inert gases have little tendency to gain or lose electrons because they are stable. Inert gases are mostly used to prevent undesirable reactions from happening due to their non-reactive properties. They are monatomic meaning they exist only as single atoms. Noble gases have their outer shells full thus cannot combine with other atoms. Alternatively diatomic gases such as nitrogen can be used where there is no reactivity with the gas being produced.

The inert gas flow control system 102 is used to control the flow of inert gas into and/or out of the chamber 120, for example to maintain the gas flow in the chamber 120 at a substantially constant level. The system comprises a control valve mounted in line for movement between open and closed positions. The gas flow control systems can be purely mechanical devices where the control member is movable from a closed position to an open position with any number of stops in between to control the flow.

Alternatively the gas flow control system 102 for controlling the flow of an inert gas to the chamber 120 may include a flow control member adapted to be mounted in line and moveable to adopt any of a plurality of positions, a gas flow indicator which produces at least one indication of the flow of the gas in the environment, and a controller which receives and acts upon the indication of the gas flow to control the position adopted by the flow control member to control the flow of the gas through the opening. The gas flow control system may control the flow of the gas to provide a desired rate of gas flow through the chamber 120. The gas flow control system may provide a substantially constant rate of gas flow through the chamber 120. The gas flow control system may provide a variable rate of gas flow through the opening. The flow control member may adopt any of a plurality of positions, ranging from and including a closed position in which the flow control member substantially closes the opening, to an open position. The controller may receive a plurality of indications of the gas flow in the environment, and may act upon each indication to control the flow of the gas through the chamber 120. The controller may establish a flow-time relationship. The controller may act upon one or more characteristics of the flow-time relationship, for example the rate of change of flow with time.

The controller may comprise or be linked to a data output display and a data input device e.g. a keypad. This enables convenient manual control of the controller, giving an easy way to set one or more operating parameters and choose one or more control characteristics. The controller may comprise or be linked to an alarm, which may be responsive to the indication of the pressure of the gas in the environment. This allows a user to be warned if necessary, for example if the gas flow in the environment exceeds or falls below a predefined level for a certain period of time. The controller may be linked to a computer system. The computer system may provide the data output display, and/or the data input device, and/or the alarm. The controller may provide data to the computer system, and may receive one or more operating signals from the computer system.

A thermally reactive mixture 110 is dispersed through a powder feed control 112 into a reaction chamber 120 that is temperature controlled using a heater 122, which may be a gas or electric furnace whose temperature can be controlled manually or by a computer.

A thermally reactive mixture consisting of Chromium Oxide, Potassium Nitrate and Sodium Nitrite in a ratio of 2:1:1 by weight was used to verify the operation of invention. This mixture generates Nitric Oxide gas that is easily analyzed using an industrial Nitric Oxide analyzer.

The powder feed control 112 can be a conveyor belt that delivers the mixture 110 into the heated chamber 120 at a predetermined rate that can be manually selected or can be computer selectable. In a belt conveyor or rope belt conveyor, an elastic and/or bendable conveyor belt is usually driven in a continuous manner by the conveyor belt being guided around return shafts or return pulleys. Here, a motor drives at least one return pulley, so that a load-bearing upper run of the conveyor belt travels in one direction, whereas a lower run travels in the opposite direction on a lower side.

Alternatively a reciprocating slide mechanism at the bottom of a powder hopper can be used to deliver a specified amount of a thermally reactive mixture 110 to the heated chamber 120. The size of the opening and the speed of the slide both in return reciprocating speed and absolute linear velocity determine the feed rate of the thermally reactive powder 110 and hence the evolution of the desired gas.

Figure 2A:
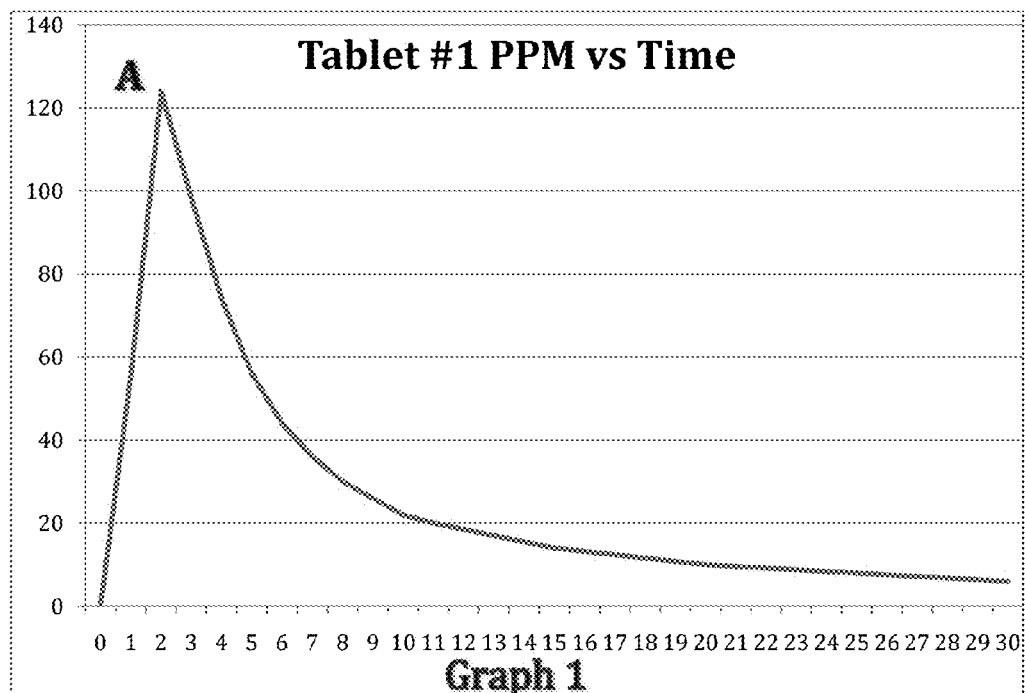
FIGS. 2A-2C show various exemplary gas release curves in accordance with one aspect of the present system.
Figure 2B:
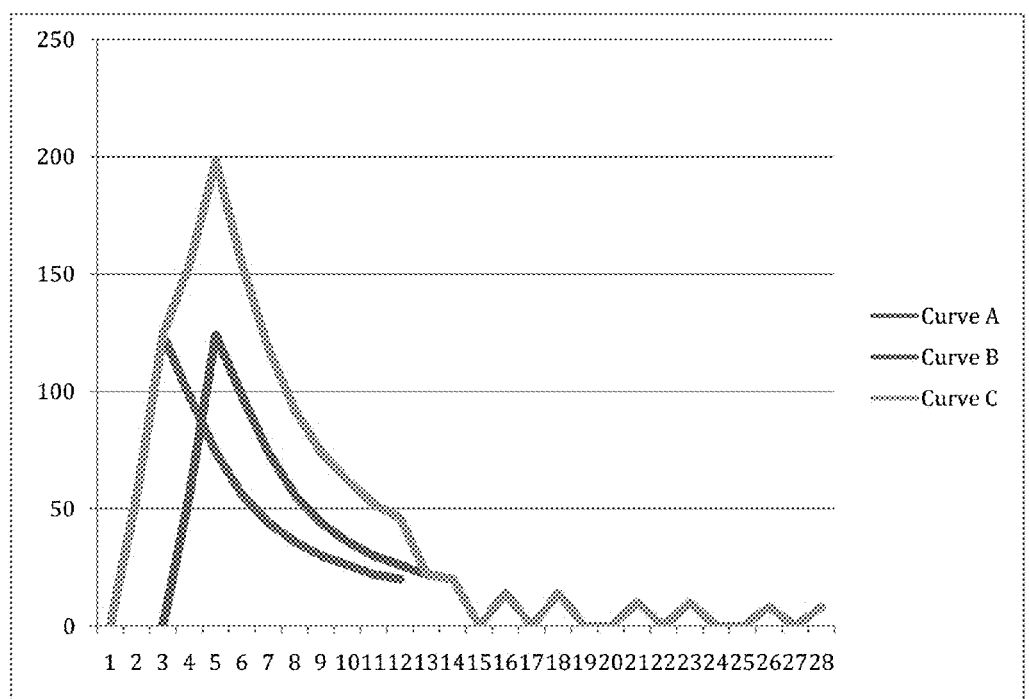
Figure 2C:
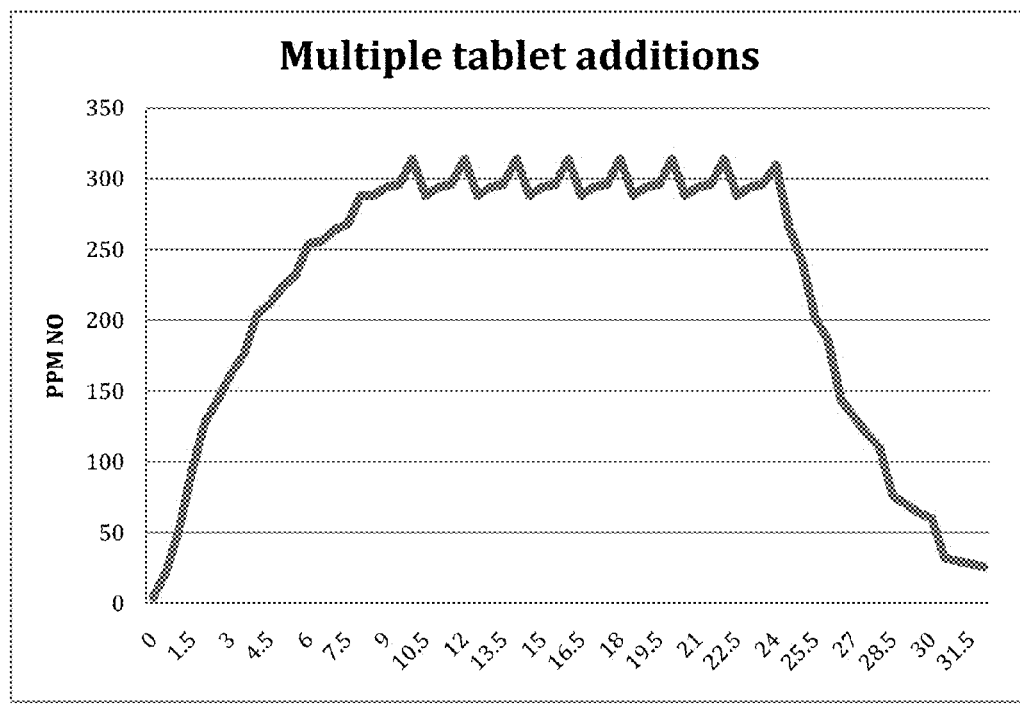

FIGS. 2A-2C show various exemplary gas release curves in accordance with one aspect of the present system. FIG. 2A shows an exemplary release of nitric oxide. This graph shows the single addition of a specified quantity and the subsequent evolution of nitric oxide gas over time. FIG. 2B shows that, if at a time at the maximum evolution of gas, time A, another equal quantity of reactive mixture is added a second curve (Curve B) of identical shape will be superimposed on the first starting at time A in FIG. 2B. The concentration of nitric oxide now will be the sum of both curves at any given time (Curve C).

FIG. 2C shows the effects of multiple tablet additions. By varying the amount of the reactant introduced and the time interval of addition and to some extent the temperature the flow of nitric oxide gas can be controlled within a specified concentration range. The initial concentration of the evolved nitric oxide gas is well above a human therapeutic level and must be diluted before it can be safely administered. A secondary dilution of the nitric oxide gas using an inert feed gas such as nitrogen is used to provide a therapeutic level of nitric oxide to the input port of a standard ventilator prior to patient inhalation.

Figure 3:
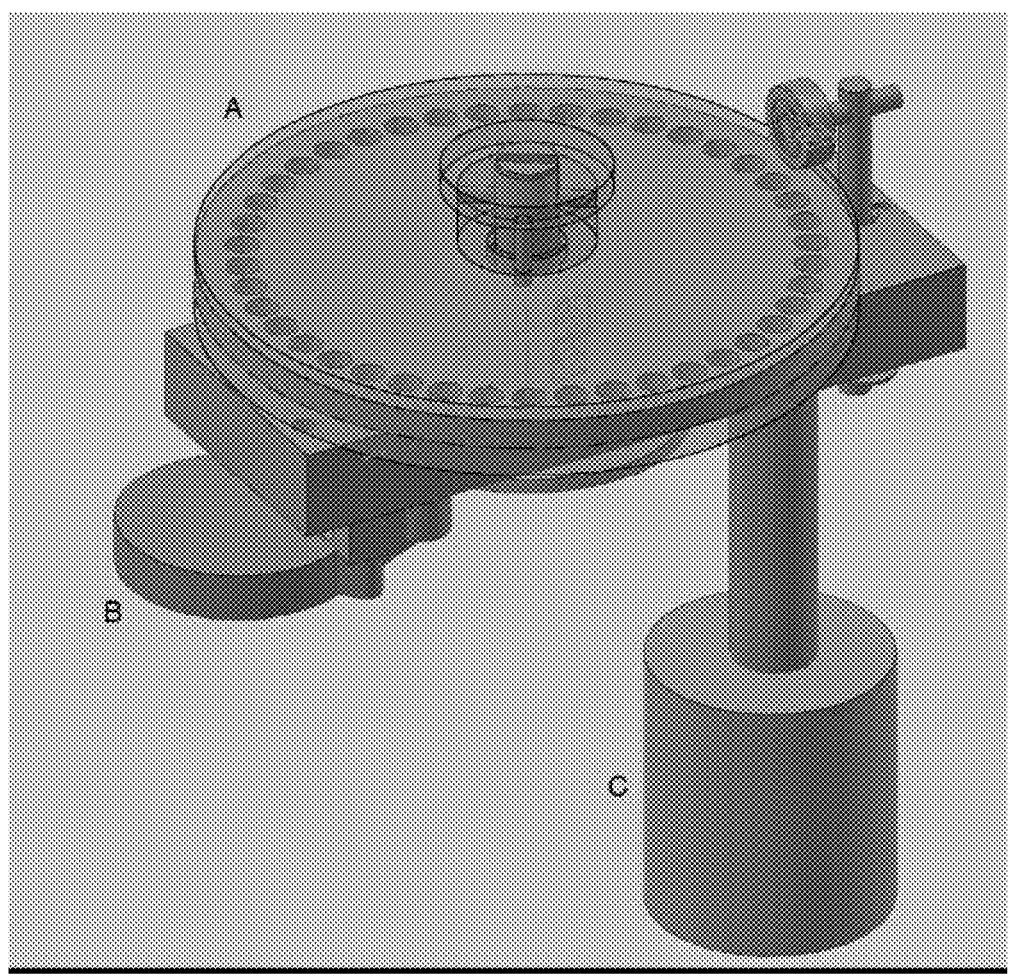
FIG. 3 shows a second exemplary system to continuously release gas.

One exemplary arrangement to achieve the gas release is illustrated in FIG. 3. The carousel A is filled with a thermally reactive mixture that will evolve pure NO gas when heated to the appropriate temperature. The carousel rotation is driven by a motor B. The carousel rotation time is controlled to drop a tablet into the furnace C at a specified time as previously discussed above.

While nitric oxide gas has been discussed as an example, the present system for continuously generating a gas from a thermally labile compound or mixture of compounds is not restricted to nitric oxide. Any gas generated can be applied to this method making it a simple, effective way of producing a gas at a specified concentration level for subsequent use in either medical or industrial applications.

Advantages of the system may include one or more of the following. The major advantages include faster reactions, cleaner products, safer reactions, quick reaction optimization, easy scale-up, and the integration of typically separate processes (such as synthesis, work-up and analysis). The system enables excellent reaction selectivity. The rapid diffusion mixing avoids the issues found in batch reactors. The high surface area to volume ratio enables almost instantaneous heating or cooling and therefore ultimate temperature control. The system allows only a small amount of hazardous intermediate to be formed at any instant. The high surface area also allows excellent control of exotherms. The system, along with automation enables the quick variation of reaction conditions. Parameters such as reaction time, temperature, ratio of reagents, concentration and reagents themselves can all be rapidly varied. One reaction can follow another, separated by solvent, each cleaning out the previous reaction. Scale up issues are minimized due to maintaining excellent mixing and heat transfer. Higher flow rates and correspondingly larger reactors can be used to easily produce kilogram quantities. The system facilitates reaction conditions not possible in batch mode.

Although various embodiments of the invention have been described, it is to be understood that they are meant to be illustrative only and not limiting. Certain features may be changed without departing from the spirit or scope of the invention. It is apparent that the present invention has broad application to the production of medically significant gases from inorganic feed material by reaction of the inorganic feed material in the presence of a catalyst at an elevated temperature. Accordingly, the invention is not to be construed as limited to the specific embodiments or examples discussed but only as defined in the appended claims or substantial equivalents thereto.

What is claimed is:

1. A gas delivery system, comprising:
   a rotatable pellet delivery carousel that drops a tablet with a thermally labile compound into a temperature controlled gas generation furnace to generate a pure gas, wherein the thermally labile compound comprises Chromium Oxide, Potassium Nitrate and Sodium Nitrite in a ratio of 2:1:1 by weight;
   a timer coupled to the carousel to control rotational timed addition of thermally labile compound to drop a pellet into the furnace and to achieve continuous evolution of gas;
   a temperature sensor to monitor the furnace temperature;
   a dispenser that provides a carrier gas to dilute the pure gas generated from a heated zone;
   a controller coupled to the carousel to control pellet feed rate;
   a controller coupled to the temperature sensor to control temperature; and
   a controller coupled to the dispenser to control inert gas flow to provide a nitric oxide concentration steady state,
   wherein each pellet results in a non-linear evolution of nitric oxide gas over time, and an evolution of nitric gas from dispensed pellets are superimposed to result in a predetermined concentration of nitric oxide.

2. The system of claim 1, further comprising a container with a carrier gas which dilutes the gas to a therapeutic dose or concentration level.

3. The system of claim 1, further comprising a container for a reactant introduction and wherein each of time interval and temperature is varied to control flow of the gas within a specified concentration range.

4. The system of claim 1, wherein an initial concentration of the generated gas is outside a human therapeutic level, comprising a module for diluting the gas before administering the gas.

5. The system of claim 4, comprising a ventilator, wherein a secondary dilution is applied to the gas to provide a therapeutic level of nitric oxide prior to patient inhalation.

* * * * *